(12) United States Patent
Ghelmansarai

(10) Patent No.: US 6,760,402 B2
(45) Date of Patent: Jul. 6, 2004

(54) VERIFICATION OF MLC LEAF POSITION AND OF RADIATION AND LIGHT FIELD CONGRUENCE

(75) Inventor: Farhad A. Ghelmansarai, Danville, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 49 days.

(21) Appl. No.: 10/211,470

(22) Filed: Aug. 1, 2002

(65) Prior Publication Data

US 2004/0022363 A1 Feb. 5, 2004

(51) Int. Cl.$^7$ .......................... A61N 5/10; G01D 18/00
(52) U.S. Cl. ...................... 378/65; 378/164; 378/206; 378/207; 250/252.1
(58) Field of Search .................. 378/65, 162, 163, 378/164, 204, 205, 206, 207; 250/252.1

(56) References Cited

U.S. PATENT DOCUMENTS

| | | | | |
|---|---|---|---|---|
| 5,052,035 A | * | 9/1991 | Krupnick | 378/163 |
| 5,684,854 A | * | 11/1997 | Hughes | 378/206 |
| 6,322,249 B1 | | 11/2001 | Wofford et al. | |
| 6,345,114 B1 | * | 2/2002 | Mackie et al. | 382/132 |
| 6,478,462 B2 | * | 11/2002 | Polkus et al. | 378/207 |
| 6,626,569 B2 | * | 9/2003 | Reinstein et al. | 378/206 |
| 2003/0185348 A1 | * | 10/2003 | Ghelmansarai | 378/206 |

OTHER PUBLICATIONS

ImPACT Information Leaflet 1: "CT Scanner Acceptance Testing", Version 1.02, May 18, 2001, © ImPACT 2001, 8pgs.

Pasma, Kasper L. et al., "Dosimetric verification of intensity modulated beams produced with dynamic multileaf collimation using an electronic portal imaging device", taken from Med. Phys. 26 (11): 2373–8, Nov. 1999. p. 93–102.
Wang, Xiaohong et al., "Dosimetric verification of intensity–modulated fields", taken from Med. Phys. 23 (3), Mar. 1996. p. 317–327.
Low, DA et al., "Phantoms for IMRT Dose Distribution Measurement and Treatment Verification", Int J Radiat Oncol Biol Phys Mar. 15, 1998; 40(5):1231–5 © 1999–2002 Varian Medial Systems, Inc., download from http://www.varian.com/onc/imr017_39.html on May 17, 2002, 1pg.
Curtin–Savard AJ et al., "Verification Of Segmented Beam Delivery Using A Commercial Electronic Portal Imaging Device", Med Phys May 1999; 26(5):737–42, © 1999–2002 Varian Medical Systems, Inc., download from http://www.varian.com/onc/imr017_38.html on May 17, 2002, 1pg.
Chang, J. et al., "Relative Profile and Dose Verification of Intensity–Modulated Radiation Therapy", Int J. Radiat. Oncol. Biol Phys Apr. 1, 2000;47(1):231–40, © 1999–2002 Varian Medical Systems, Inc., download from http://www.varian.com/onc/imr01736.html on May 17, 2002, 1pg.

(List continued on next page.)

Primary Examiner—Edward J. Glick
Assistant Examiner—Allen C. Ho

(57) ABSTRACT

A system includes acquisition of first electronic image data representing a phantom located at a first position and irradiated by a first radiation field emitted by a radiation emitter, acquisition of second electronic image data representing the phantom located at a second position based at least on a first light field emitted by a light emitter and irradiated by a second radiation field emitted by the radiation emitter, generation of third electronic image data by correcting the second electronic image data based at least on the first electronic image data, and determination of a deviation between the first light field and the second radiation field based at least on the third electronic image data.

26 Claims, 17 Drawing Sheets

OTHER PUBLICATIONS

Mick Radio–Nuclear Instruments, Inc., "Quality Assurance Tools: PermaDoc Phantom", Catalog #9404, Patent #5,561,698 download from http://www.micknuclear.com/page13.html on May 21, 2002, 3pgs.

Mick Radio–Nuclear Instruments, Inc., "Quality Assurance Tools, IBC II: Isocentric Beam Checker II", Catalog #9116 download from http://www.micknuclear.com/page16.html on May 21, 20002, 3pgs.

Mick Radio–Nuclear Instruments, Inc., "Quality Assurance Tools, IBC I: Isocentric Beam Checker I", Catalog #7801 download from http://www.micknuclear/page15.html on May 21, 2002, 4 pgs.

* cited by examiner

VERIFICATION OF MLC LEAF POSITION AND OF RADIATION AND LIGHT FIELD CONGRUENCE

BACKGROUND

1. Field

The present invention relates generally to radiation treatment, and more particularly to calibrating systems to be used during such treatment.

2. Description

Conventional radiation treatment typically involves directing a radiation beam at a tumor in a patient to deliver a predetermined dose of treatment radiation to the tumor according to an established treatment plan. A suitable radiation treatment device is described in U.S. Pat. No. 5,668,847, issued Sep. 16, 1997 to Hernandez, the contents of which are incorporated herein for all purposes.

Healthy tissue and organs are often in the treatment path of the radiation beam during radiation treatment. The healthy tissue and organs must be taken into account when delivering a dose of radiation to the tumor, thereby complicating determination of the treatment plan. Specifically, the plan must strike a balance between the need to minimize damage to healthy tissue and organs and the need to ensure that the tumor receives an adequately high dose of radiation. In this regard, cure rates for many tumors are a sensitive function of the radiation dose they receive.

Treatment plans are therefore designed to maximize radiation delivered to a target while minimizing radiation delivered to healthy tissue. If the radiation is not delivered exactly as required by the treatment plan, the goals of maximizing target radiation and minimizing healthy tissue radiation may not be achieved. More specifically, errors in radiation delivery can result in low irradiation of tumors and high irradiation of sensitive healthy tissue. The potential for mis-irradiation increases with increased delivery errors.

To ensure that radiation will be delivered to a proper area, a light field is used to indicate the position of a field within which radiation will be delivered. In particular, light is projected onto a patient to create a light field and an operator determines whether the light field delineates an area to which radiation is to be delivered according to a treatment plan. Accordingly, the light field is assumed to be located at a same position as a radiation field within which radiation will be delivered during radiation treatment.

Delivery errors may occur if the light field is not located at a same position as the subsequently-produced radiation field. Accordingly, it is necessary to verify that the position of the light field accurately represents a position of the radiation field. Conventional verification procedures are time-consuming. Accordingly, an operator may verify congruence of the light field and the radiation field only at the beginning of each day. As a result, the operator is not aware if the light field and the radiation field have become misaligned at some point during the day and each subsequent patient during the day is exposed to the possibility of increased delivery errors.

Modern radiation therapy uses beam-shaping devices to produce radiation fields of various shapes. These radiation fields may be used to provide more precise treatment than otherwise available. In order to avoid irradiation of unintended targets by a shaped radiation field, an operator verifies that the beam-shaping devices are configured so as to produce a field shape that complies with a specified treatment plan. As described above, current procedures for verifying the configuration of beam-shaping devices are slow and therefore performed at unacceptable intervals, such as daily.

It would therefore be beneficial to provide efficient and effective verification of congruence between a light field and a radiation field used for radiation treatment, as well as verification of beam-shaping device configuration. When used in conjunction with conventionally-designed treatments, such verification could reduce the chance of harming healthy tissue. Such verification may also allow the use of more aggressive treatments than currently available.

SUMMARY

To address at least the above problems, some embodiments of the present invention provide a system, method, apparatus, and means to acquire first electronic image data representing a phantom located at a first position and irradiated by a first radiation field emitted by a radiation emitter, acquire second electronic image data representing the phantom located at a second position based at least on a first light field emitted by the light emitter and irradiated by a second radiation field emitted by the radiation emitter, generate third electronic image data by correcting the second electronic image data based at least on the first electronic image data, and determine a deviation between the first light field and the second radiation field based at least on the third electronic image data.

In some embodiments, the present invention provides acquisition of first electronic image data representing a first radiation field emitted by a radiation emitter and shaped by one or more of multi-leaf collimator leaves in a first leaf configuration, movement of one or more of the multi-leaf collimator leaves from the first leaf configuration, movement of one or more of the multi-leaf collimator leaves to a second leaf configuration, acquisition of second electronic image data representing a second radiation field emitted by a radiation emitter and shaped by one or more of the multi-leaf collimator leaves in the second leaf configuration, generation of third electronic image data by correcting the second electronic image data based at least on the first electronic image data, and determination of a deviation between the first radiation field and the second radiation field based at least on the third electronic image data.

The present invention is not limited to the disclosed embodiments, however, as those of ordinary skill in the art can readily adapt the teachings of the present invention to create other embodiments and applications.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts, and wherein.

DETAILED DESCRIPTION

The following description is provided to enable any person of ordinary skill in the art to make and use the invention and sets forth the best modes contemplated by the inventor for carrying out the invention. Various modifications, however, will remain readily apparent to those in the art.

Figure 1:
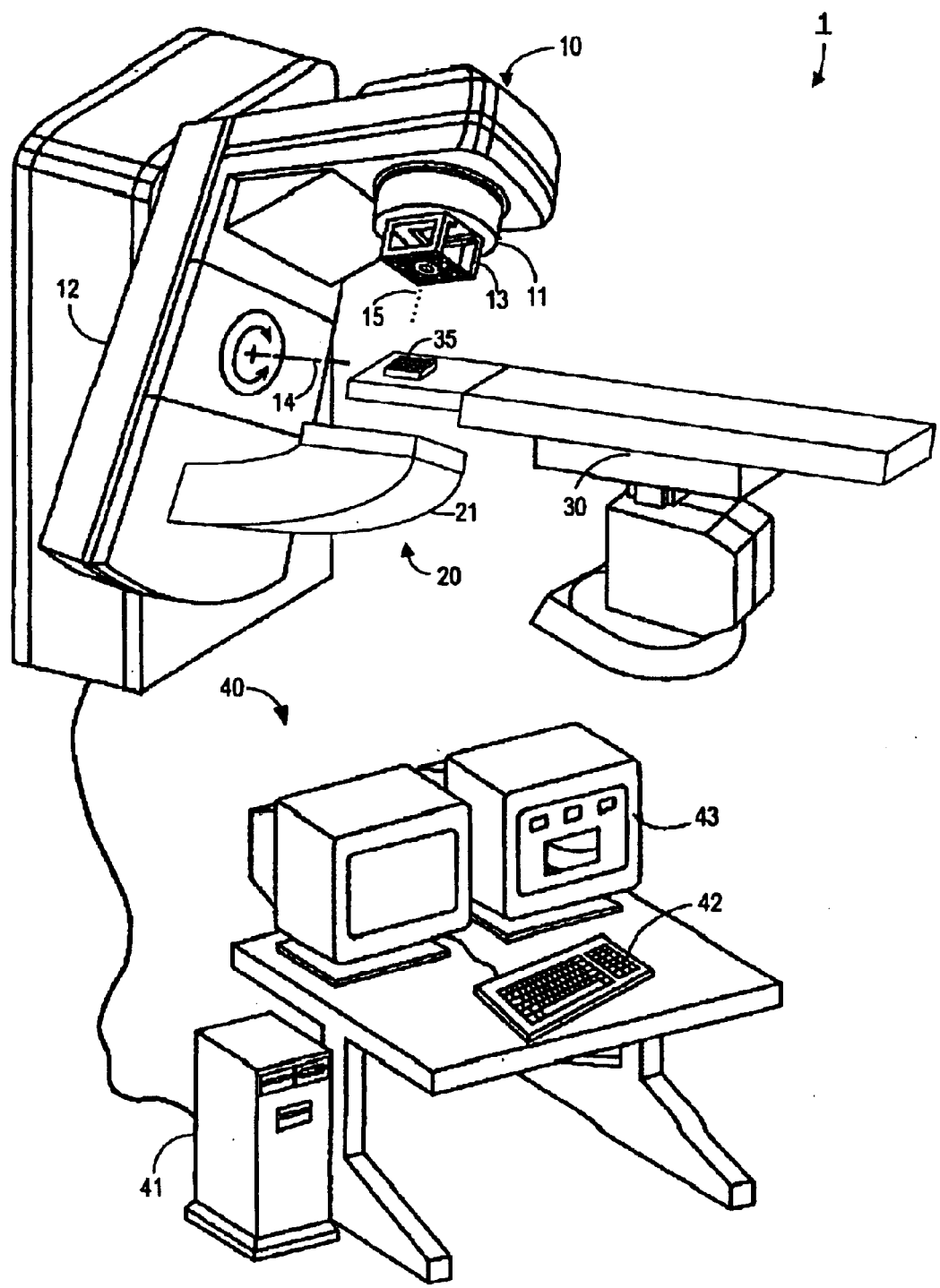
FIG. 1 is diagram illustrating a radiation treatment room according to some embodiments of the present invention.

FIG. 1 illustrates radiation treatment room 1 pursuant to some embodiments of the present invention. Radiation treatment room 1 includes linear accelerator (linac) 10, imaging device 20, treatment table 30 and operator station 40. The elements of radiation treatment room 1 are used to deliver treatment radiation to a patient according to a radiation treatment plan.

Linac 10 delivers treatment radiation to a treatment area and is primarily composed of treatment head 11 and gantry 12. Treatment head 11 includes a beam-emitting device for emitting treatment radiation used during calibration and/or treatment. The treatment radiation may comprise electron, photon or any other type of radiation. Treatment head 11 also includes a light-emitting device such as a light bulb. The light bulb is used to produce a light field for confirming a location of a radiation field to be delivered. In this regard, the term "light" will be used to describe the radiation emitted from the light bulb and used to produce a light field. On the other hand, the terms "treatment radiation" and "radiation" will be used herein to identify radiation emitted by the beam-emitting device.

Also included within treatment head 11 are two sets of opposing jaws used to define a light field and a radiation field produced by linac 10. Disposed between the jaws and table 30 is a multi-leaf collimator for shaping any radiation and light that is emitted by the beam-emitting device and the light bulb and that passes through an opposing set of jaws. The arrangement of the jaws and the collimator according to some embodiments of the invention is described in more detail below with respect to FIG. 2.

Accessory tray 13 is mounted on treatment head 11 and may be configured to receive and securely hold attachments used during the course of treatment planning and treatment. These attachments may include reticles, wedges, or the like for further defining field sizes and intensities.

Treatment head 11 is fastened to a projection of gantry 12. Gantry 12 is rotatable around gantry axis 14 before, during and after radiation treatment. During such treatment, radiation is delivered from linac 10 to the beam-emitting device of treatment head 11 and emitted therefrom along beam axis 15. The delivered radiation is centered on a point, known as the isocenter, which is located at the intersection of beam axis 15 and gantry axis 14. It should be noted that, due to divergence of the emitted radiation and shaping of the radiation by the jaws and/or collimator leaves, the radiation is delivered to a radiation field rather than only to the point upon which the radiation is centered.

Imaging device 20 acquires images that are used before, during and after radiation treatment. For example, imaging device 20 is used to acquire images for verification and recordation of a patient position and of an internal patient portal to which radiation is delivered. Images acquired by imaging device 20 may also be used according to some embodiments of the invention to verify congruence of a light field and a radiation field produced by linac 10 and/or to verify the configuration of the leaves of the collimator. As described above, the effectiveness of radiation treatment often depends on the accuracy of the congruence and the leaf configuration. Examples of techniques for verifying field congruence and for verifying leaf configuration according to some embodiments of the invention are set forth in detail below.

In some embodiments, imaging device 20 comprises light-proof housing 21 within which are disposed a scintillator, a mirror and a CCD or tube-based camera. Generally, imaging device 20 may be used to acquire images of items irradiated by light and/or treatment radiation. Housing 21 may be attached to gantry 12 in any manner, and may include an extendible and retractable structure. According to some embodiments, imaging device 20 comprises the BEAMVIEW™ system produced by the present assignee. Further details of the structure and operation of imaging device 20 according to some embodiments of the invention are set forth below with respect to FIGS. 3 and 4.

Table 30 supports a patient during radiation treatment. Table 30 is adjustable to ensure, along with rotation of gantry 12, that an area of the patient that is to be treated is positioned at the isocenter. In this regard, located at the isocenter of linac 10 in FIG. 1 is phantom 35. Phantom 35 is used as described below to verify congruence between a light field and a radiation field produced by linac 10 and/or to verify the configuration of the leaves of the collimator. Phantom 35 may be placed on top of, affixed to, or embedded in table 30. The properties of phantom 35 will be discussed with respect to FIG. 5.

Operator station 40 includes a processor 41 in communication with an input device such as keyboard 42 and an operator console 43 (including one or more visual display units or monitor). Operator station 40 is typically operated by an operator who administers actual delivery of radiation treatment as prescribed by an oncologist. Operator station 40 may be located apart from linac 10, such as in a different room, in order to protect the operator from radiation. For example, linac 10 may be located in a heavily shielded room, such as a concrete vault, which shields the operator from radiation generated by linac 10.

The operator uses keyboard 42 to perform calibration procedures including verification of field congruence, verification of leaf configuration, and acquisition of data used for image correction, to input data defining a radiation dose to be delivered to the patient, and to deliver treatment radiation to the patient. The data may also be input via another input device, such as a data storage device. Operator console 43 displays data to the operator before, during and after the treatment.

Processor 41 may store processor-executable process steps according to some embodiments of the present invention. In some aspects, the process steps are executed by processor 41, linac 10, imaging device 20, and/or another device to acquire first electronic image data representing a phantom located at a first position and irradiated by a first radiation field emitted by a radiation emitter, acquire second electronic image data representing the phantom located at a second position based at least on a first light field emitted by the light emitter and irradiated by a second radiation field emitted by the radiation emitter, generate third electronic image data by correcting the second electronic image data based at least on the first electronic image data, and determine a deviation between the first light field and the second radiation field based at least on the third electronic image data.

The process steps may also provide acquisition of first electronic image data representing a first radiation field emitted by a radiation emitter and shaped by one or more of multi-leaf collimator leaves in a first leaf configuration, movement of one or more of the multi-leaf collimator leaves from the first leaf configuration, movement of one or more of the multi-leaf collimator leaves to a second leaf configuration, acquisition of second electronic image data representing a second radiation field emitted by a radiation emitter and shaped by one or more of the multi-leaf collimator leaves in the second leaf configuration, generation of third electronic image data by correcting the second electronic image data based at least on the first electronic image data, and determination of a deviation between the first radiation field and the second radiation field based at least on the third electronic image data.

The above-described steps may also be embodied, in whole or in part, by hardware of processor 41, linac 10, imaging device 20. Moreover, embodiments of the invention may be embodied by hardware and/or software of a standalone device connected between imaging device 20 and operator station 40, between linac 10 and imaging device 20, or elsewhere.

Of course, each of the devices shown in FIG. 1 may include less or more elements than those shown. Moreover, transformation and storage of acquired data may be performed by any one or more of the devices. In addition, embodiments of the invention are not limited to the devices shown.

Figure 2:
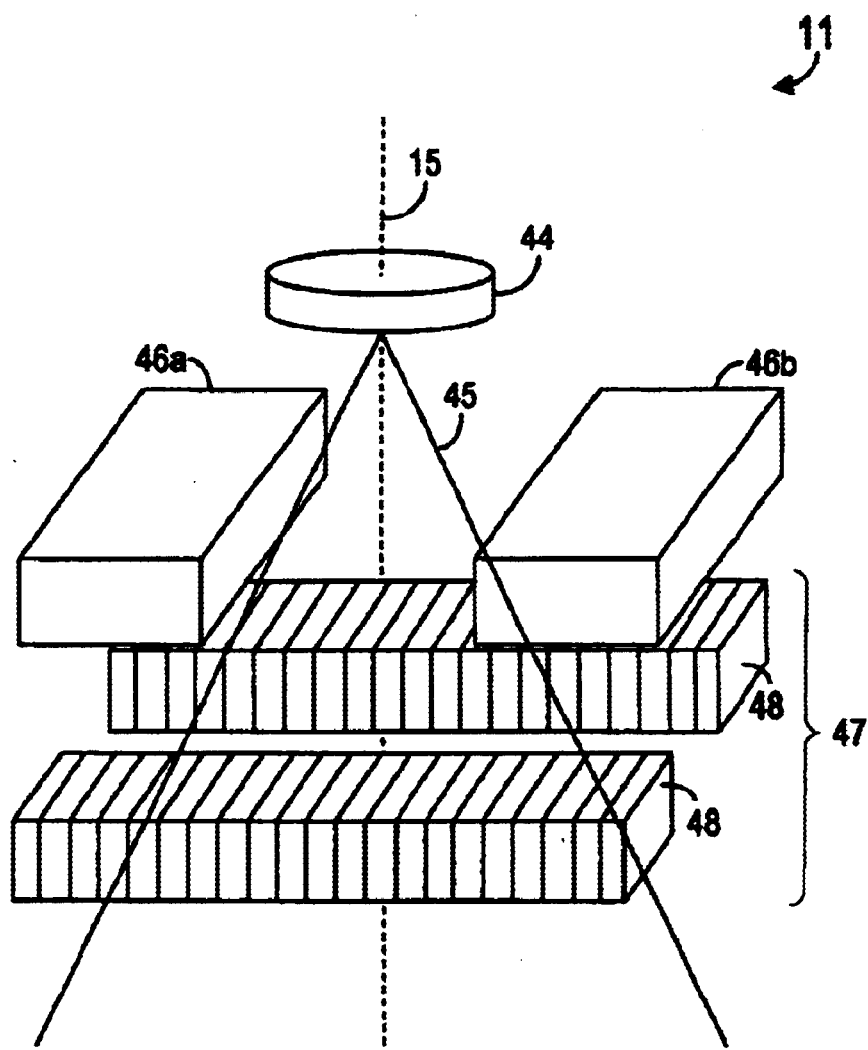
FIG. 2 is a diagram illustrating elements of a treatment head according to some embodiments of the present invention.

FIG. 2 is a representative view of elements of treatment head 11 according to some embodiments of the present invention. As shown, a radiation and/or light beam travels along beam axis 15 toward lens 44 of treatment head 11. Lens 44 is used to spread the beam into conical path 45 having an axis along beam axis 15.

Jaws 46*a* and 46*b* are movable along a first dimension in order to shape the spread beam in the first dimension. Multi-leaf collimator 47 consists of two sets of leaves 48. Each of leaves 48 is independently movable along a second dimension perpendicular to the first dimension in order to shape a beam that has passed through jaws 46*a* and 46*b*. In one example of operation of collimator 47, jaws 46*a* and 46*b* are moved to provide a maximum distance there between so as to allow the first dimension of the beam to be determined completely by leaves 48. It should be noted that any currently or hereafter-known multi-leaf collimator and configuration of treatment head elements may be used in conjunction with some embodiments of the invention.

Figure 3:
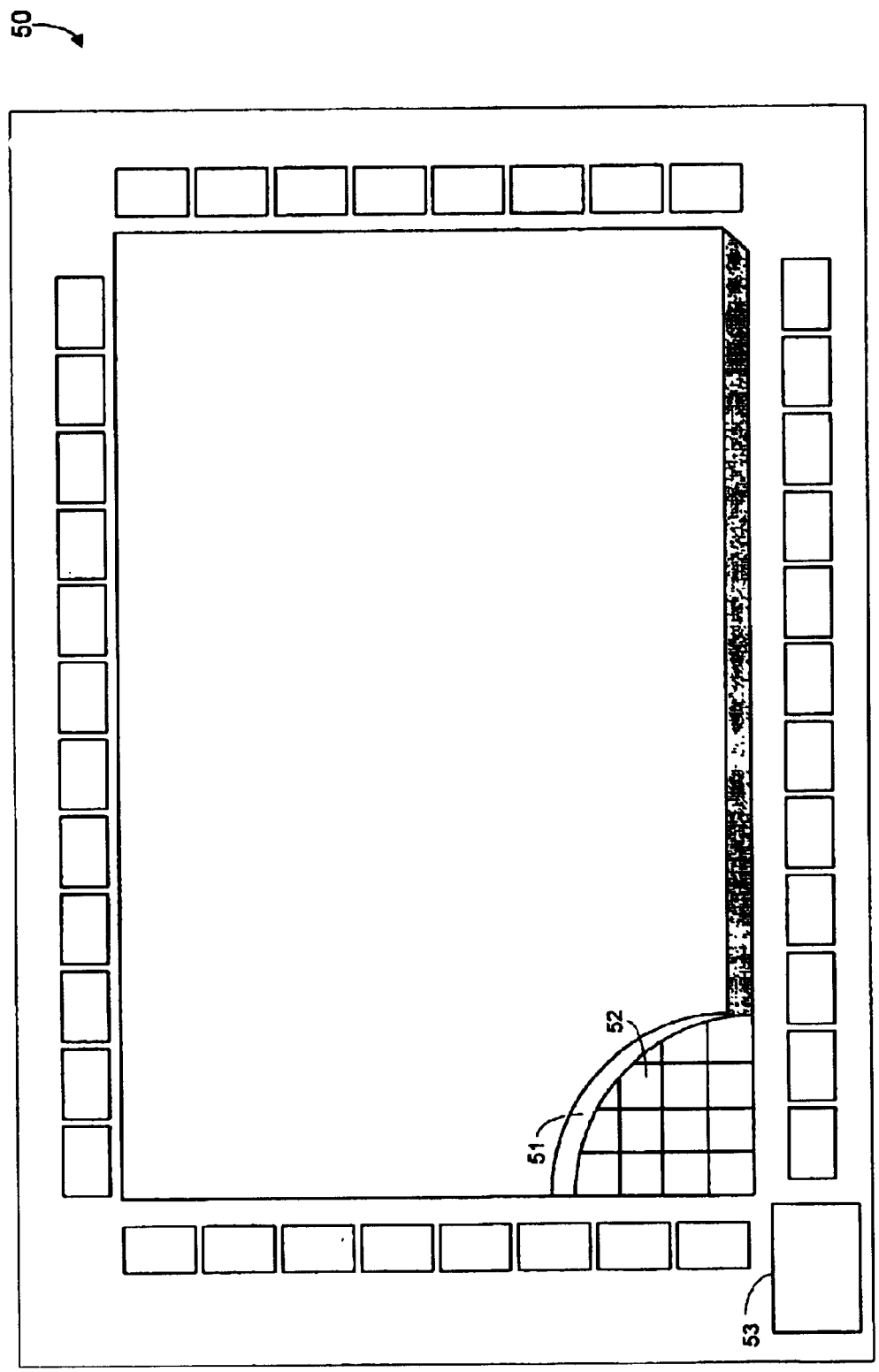
FIG. 3 is a diagram illustrating elements of an imaging device according to some embodiments of the present invention.

FIG. 3 is an illustration of electronic flat panel 50 of imaging device 20 according to some embodiments of the invention. Flat panel device 50 is positioned at an upper portion of imaging device 20 so as to allow radiation produced by linac 10 to pass through a patient or phantom and to be absorbed by scintillator 51. Scintillator 51 is a gadolinium-sulfide layer that absorbs x-ray radiation and emits visible photons having an intensity proportional to that of the absorbed x-rays. Other types of scintillators usable for indirect detection include Cesium-iodide or Lanex™ fast scintillators. For illustrative purposes, a portion of scintillator 51 is cut away to show imaging elements 52.

Briefly, photodiodes of imaging elements 52 absorb visible photons generated by scintillator 51 and the absorbed photons generate a current that is integrated into the photodiodes' self-capacitance as an electrical charge. The electrical charge stored in a photodiode is therefore proportional to an intensity of x-rays absorbed by a portion of scintillator 51 that lies above the photodiode. The charge is read from the photodiode by applying a signal to a transistor associated with the photodiode and the read charge may be used to construct an image. Accordingly, flat panel 50 is known as a CCD-based imaging device.

Timing and control IC 53 controls operation of flat panel 50 in accordance with process steps stored therein and commands received from remotely connected devices such as linac 10 or processor 41. Commands and data can be transmitted to and from flat panel 50 via I/O lines (not shown). Moreover, the elements of flat panel 50 may be encased in a suitable protective housing.

Figure 4:
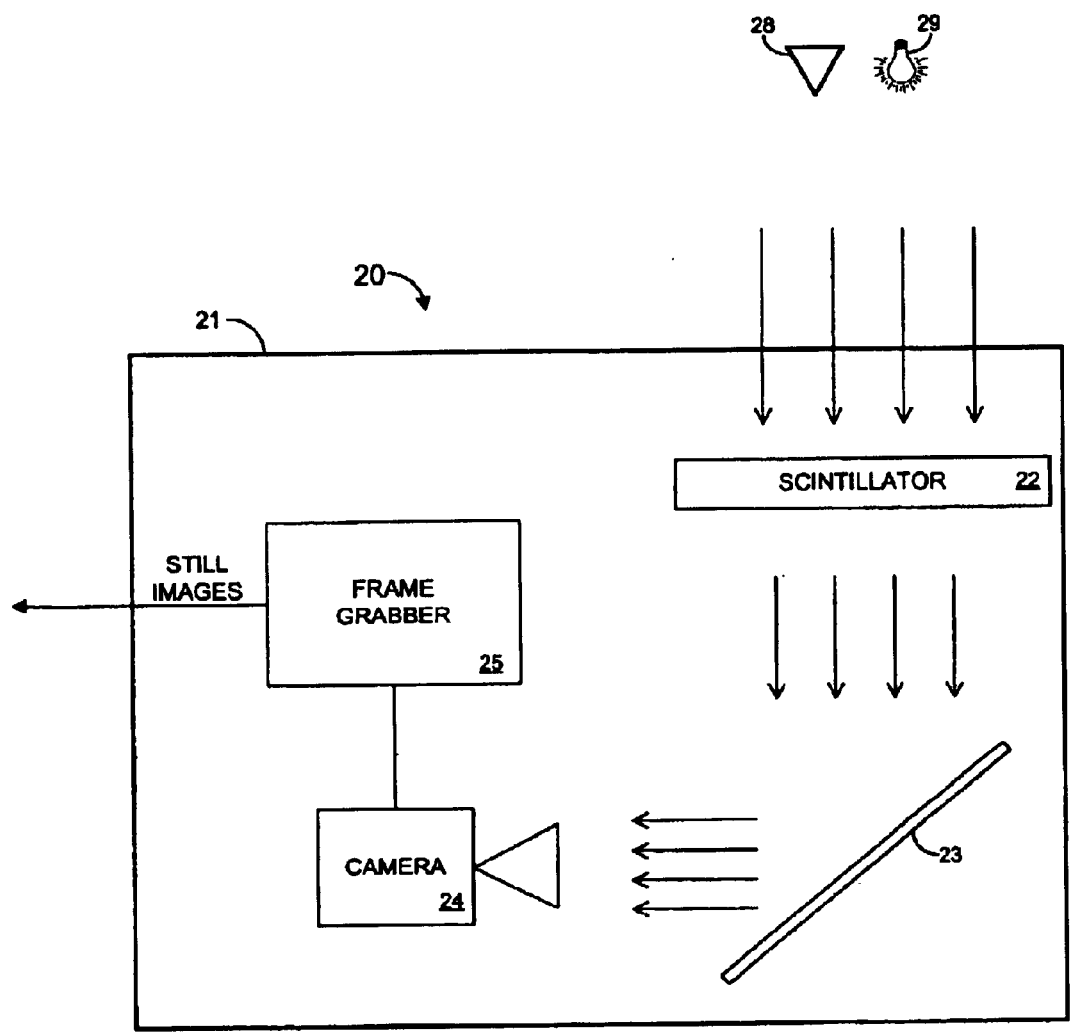
FIG. 4 is a diagram illustrating elements of an imaging device according to some embodiments of the present invention.

FIG. 4 is a diagram illustrating elements of imaging device 20 according to some other embodiments of the invention. As shown, imaging device 20 consists of housing 21, scintillator 22, mirror 23, tube-based camera 24, and frame grabber 25. Housing 21 is designed so that no light can enter imaging device 20 when scintillator 22 is in the position shown. In this regard, also shown in FIG. 4 are treatment radiation emitter 28 and light bulb 29, both of which are disposed within treatment head 11.

As described with respect to FIG. 3, scintillator 22 absorbs treatment radiation emitted by treatment radiation emitter 28 and emits visible photons having an intensity proportional to that of the absorbed radiation toward mirror 23. Accordingly, the photons are reflected toward camera 24, thereby allowing camera 24 to acquire an image representing a radiation field produced by radiation emitter 28. Such an image would also represent any object that is not completely transparent to the treatment radiation and that is placed between radiation emitter 28 and scintillator 22.

Imaging device 20 also includes frame grabber 25 to read a video signal output by camera 24 in real-time and to produce still frames therefrom. Still frame images may be output from imaging device 20 to acquisition and image processing software executed by processor 41 or by another device and may alternatively or additionally be output to an operator through console 43.

In some embodiments, the scintillators of the imaging devices of FIGS. 3 and 4 may be moved manually or using hardware and/or software so that light emitted by light bulb 29 can pass directly to mirror 23. This light is then reflected toward camera 24, enabling camera 24 to acquire an image representing a light field produced by light bulb 29. As a result, a radiation image and a light image of an object may be obtained without changing a physical relationship between the object and imaging device 20. As will be evident from the foregoing description, some embodiments of the invention are particularly useful in conjunction with imaging devices that cannot move their scintillators in this manner.

Figure 5:
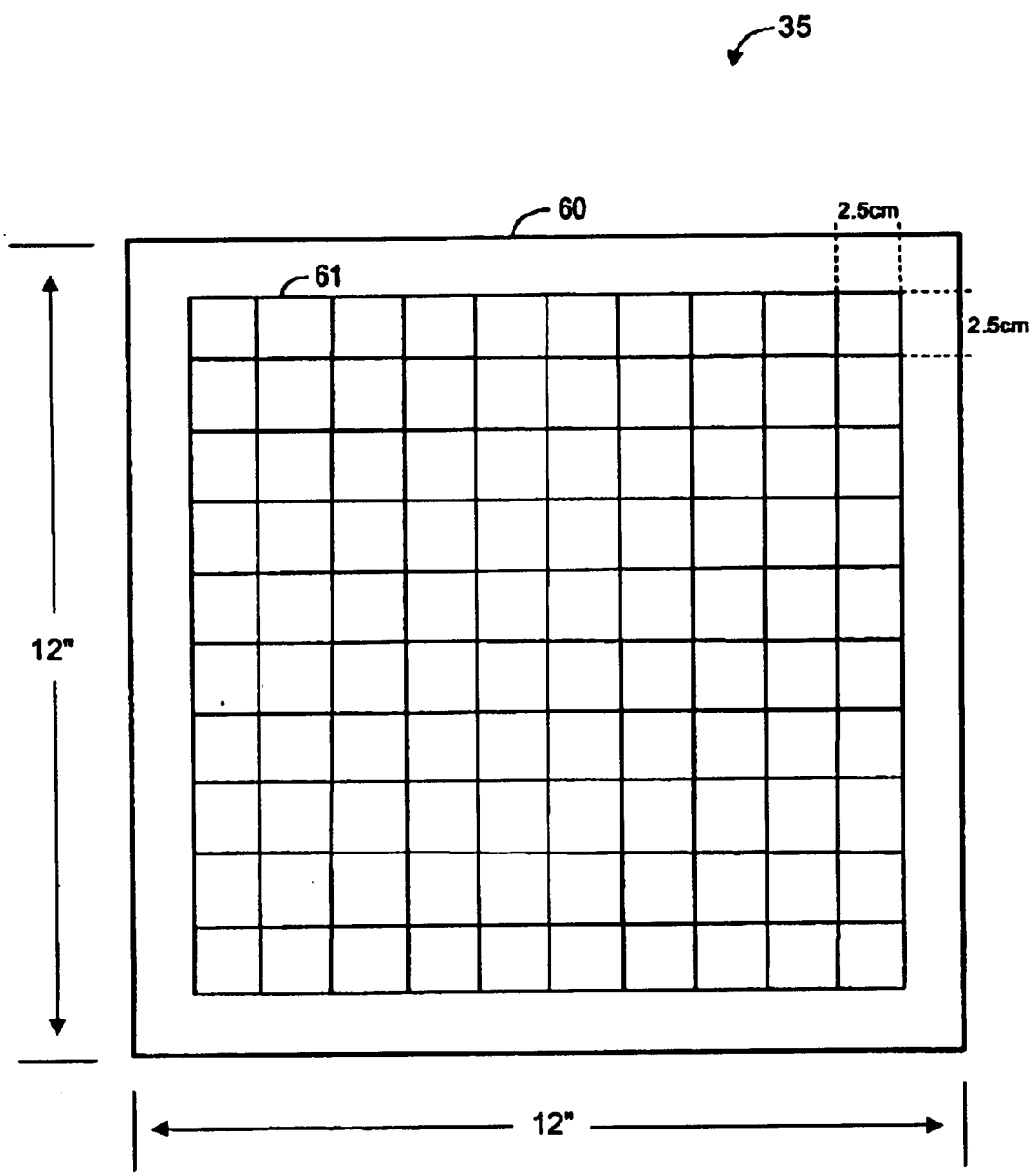
FIG. 5 is a view of a phantom used in conjunction with some embodiments of the present invention.

FIG. 5 is a representative top view of phantom 35 according to some embodiments of the invention. Phantom 35 of FIG. 5 is comprised of 12 in×12 in square substrate 60 in which is embedded wire frame 61. Wire frame 61 is formed in a grid pattern comprising one hundred 2.5 cm×2.5 cm squares. It should be noted that substrate 60 and frame 61 may each be composed of any two materials having different radiation attenuation characteristics and which therefore appear differently from one another in a radiation image. In some embodiments, substrate 60 is composed of glass and frame 61 is composed of tungsten wire.

It should also be noted that a phantom in accordance with some embodiments of the invention may include any pattern. In some embodiments, a suitable pattern is one in which an image can be created by misalignedly superimposing the pattern onto itself, and an extent of the misalignment can be determined from the image. Phantom 35 may also be shaped or sized differently from that shown in FIG. 5. In this regard, use of larger sizes may provide the option of verifying the congruence or shape of larger radiation and/or light fields.

Figure 6A:
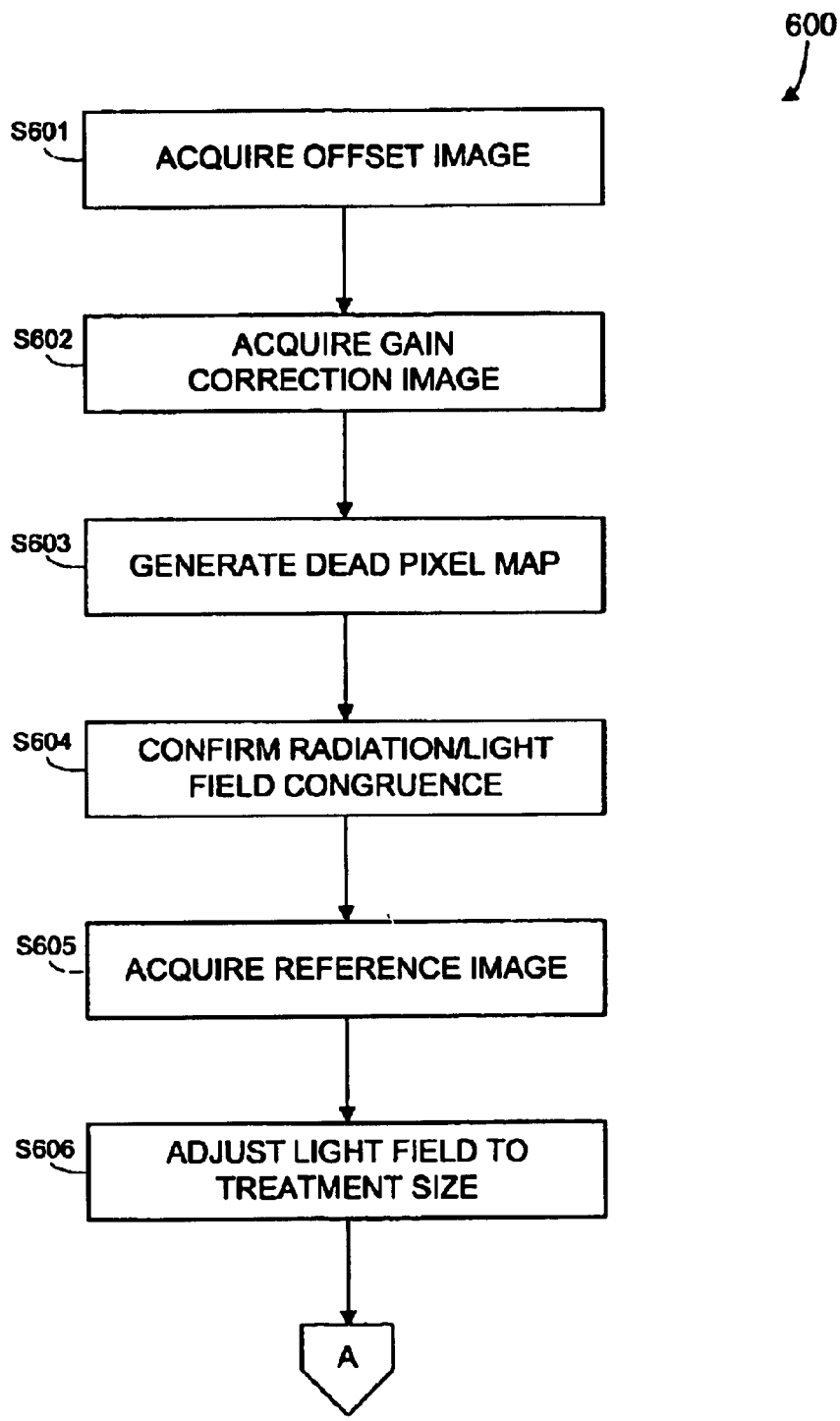
FIGS. 6A and 6B comprise a flow diagram illustrating process steps to verify radiation and light field congruence according to some embodiments of the present invention.
Figure 6B:
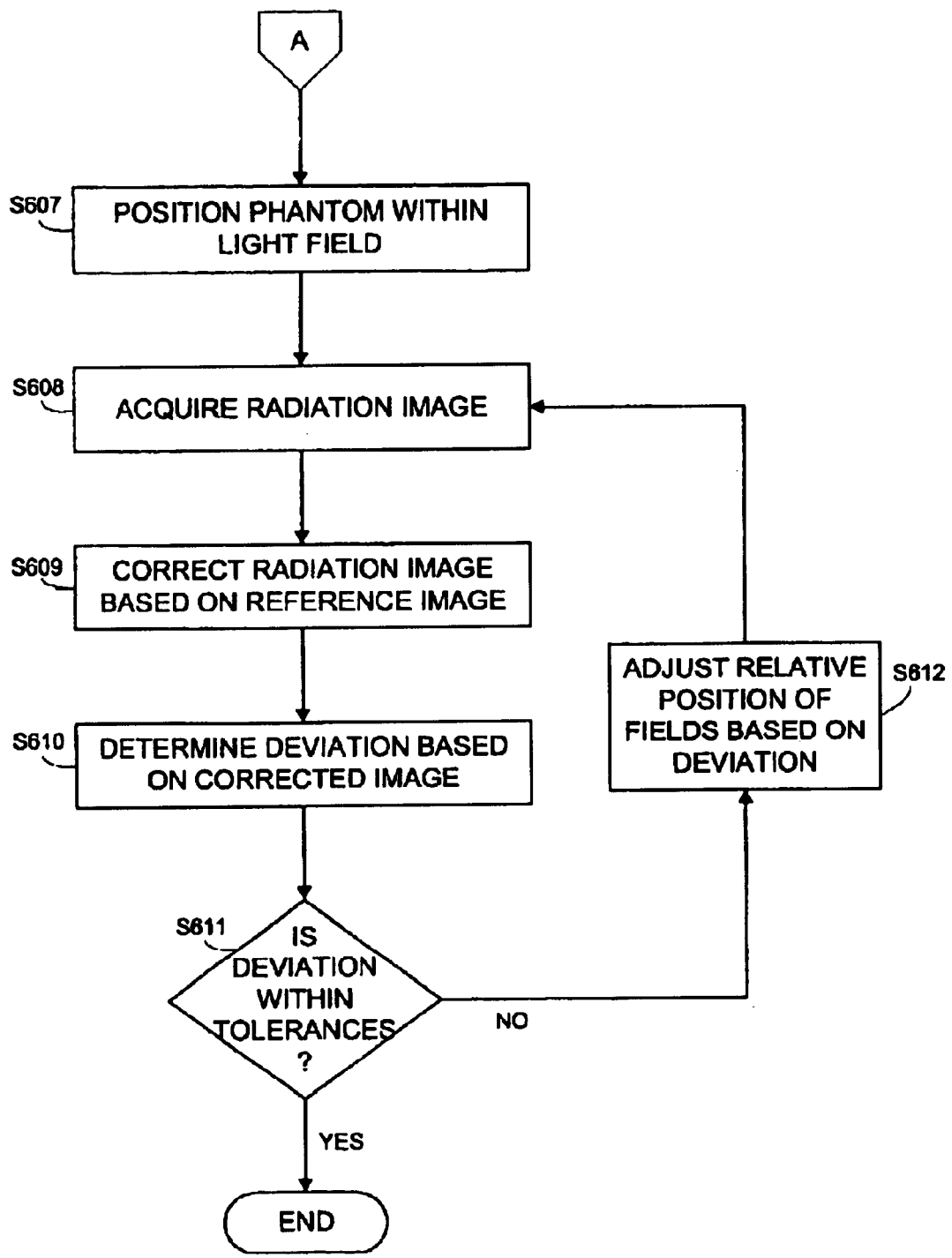

FIGS. 6A and 6B comprise a flow diagram of process steps 600 according to some embodiments of the invention. Process steps 600 may be embodied by hardware and/or software of processor 41, linac 10, imaging device 20, and/or another device in direct or indirect communication with imaging device 20. Briefly, process steps 600 provide for verifying the congruence of a light field and a radiation field prior to radiation treatment.

Process steps 600 begin at step S601, in which an offset image is acquired. In this regard, all the images acquired according to the present example of process steps 600 are acquired in the form of electronic image data. An offset image is used to reduce dark current effects experienced by some flat panel imaging devices such as flat panel 50. To obtain an offset image, image frames are acquired during a period of non-irradiation at a frame time to be used during radiation treatment, and an average image frame is calculated from the acquired frames.

Next, in step S602, a gain correction image is acquired. A gain correction image is obtained in step S602 by irradiating imaging device 20 with a uniform radiation field while no object lies between radiation emitter 28 and imaging device 20. Accordingly, variations in the pixel values of the gain correction image reflect differences in sensitivity and gain among imaging elements of an imaging device used to obtain the radiation image.

The obtained gain correction image is used in step S603 to identify non-functioning pixels of imaging device 20, or "dead" pixels. An image, or map, is generated based on the identified dead pixels and the map is used after radiation images are obtained to reassign the value of each dead pixel in an image to a value that is based on values of neighboring pixels. The images and map acquired in steps S601 through S603 are used to correct subsequently-acquired radiation images for the defects described above.

It should be noted that steps S601 and S603 might not be performed in a case that imaging device 20 is a camera-based device such as that illustrated in FIG. 4. Moreover, although a gain correction image may be acquired in step S602 in conjunction with a camera-based imaging device, such correction is most commonly used in conjunction with a flat panel imaging device. When a camera-based imaging device is used, the image acquired in step S602 may be used for shade correction instead of for gain correction image.

Congruence of a light field and a radiation field produced by linac 10 is confirmed in step S604. Conventionally, this confirmation is performed by moving collimator 47 and jaws 46a and 46b to produce a light field of a specific size and shape (e.g., square), illuminating X-ray film with the light field, marking the film at the edges of the light field illuminated thereon, exposing the film to radiation, and comparing the location of the radiation field as appearing on the exposed film with the location of the marks.

Other systems to verify congruence between the light field and the radiation field may be used in step S604, including those proposed by Luchka et al, "Assessing radiation and light field congruence with a video-based electronic portal imaging device", Med. Phys 23 (7), July 1996, pgs 1235–1252, and by Kirby, "A multipurpose phantom for use with electronic portal imaging devices", Phys. Med. Biol. 40, 1995, pgs. 323–334, as well as any other currently or hereafter-known systems.

Phantom 35 is then placed on table 30 and at the isocenter of linac 10 in step S605. The isocenter may be located by referring to marks on table 30 or by aligning lines of grid pattern 61 with a correspondingly-sized light field emitted by treatment head 11 and centered at the isocenter. A radiation image of the phantom is acquired using a radiation field that is identical to or different from the radiation field used in step S604 to confirm congruence.

Figure 7:
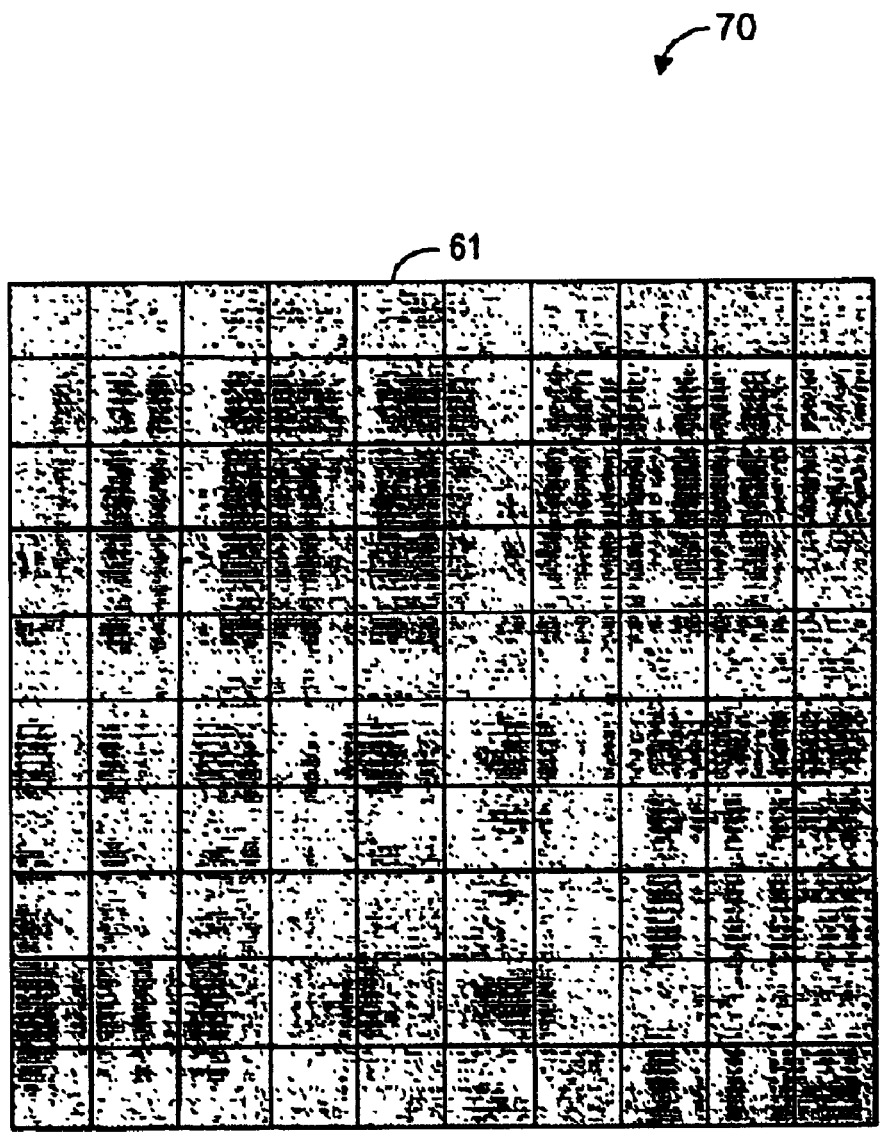
FIG. 7 is a view of a reference radiation image according to some embodiments of the present invention.

FIG. 7 is a view of reference radiation image 70 acquired according to some embodiments of step S605. A 25 cm×25 cm radiation field was used to acquire image 70, which shows wire grid pattern 61 in contrast to material of substrate 60. It should be noted that Steps S601 through S605 may be performed anytime before radiation treatment, but are commonly obtained in the early morning prior to the administration of several radiation treatments throughout the day.

Accordingly, a long delay may occur between step S605 and subsequent process steps of process steps 600. Testing, training and/or treatment may occur during this delay, in which jaws 46a and 46b may be moved, collimator leaves 48 may be moved, and gantry 12 may be rotated. As a result, efficient verification of continued congruence between the light field and the radiation field may be desired.

In step S606, jaws 46a and 46b and collimator leaves 48 are moved to adjust a size of a light field emitted from treatment head 11 to a desired size. The desired size may be dictated by a treatment plan associated with an upcoming treatment. In the present example, the size is 25 cm×25 cm, but the size need not be identical to the light field size used in step S604.

Phantom 35 is positioned within the light field in step S607. Again, markings on table 30 or wire grid pattern 61 may be used to position phantom 35 at the isocenter of linac 10 in step S607. In some embodiments, phantom 35 is not positioned at the isocenter in step S607 and, more particularly, is not positioned at the location where phantom 35 was positioned in step S605. In these embodiments, a physical relationship between the locations of the phantom in step S605 and in step S607 is known.

Figure 8:
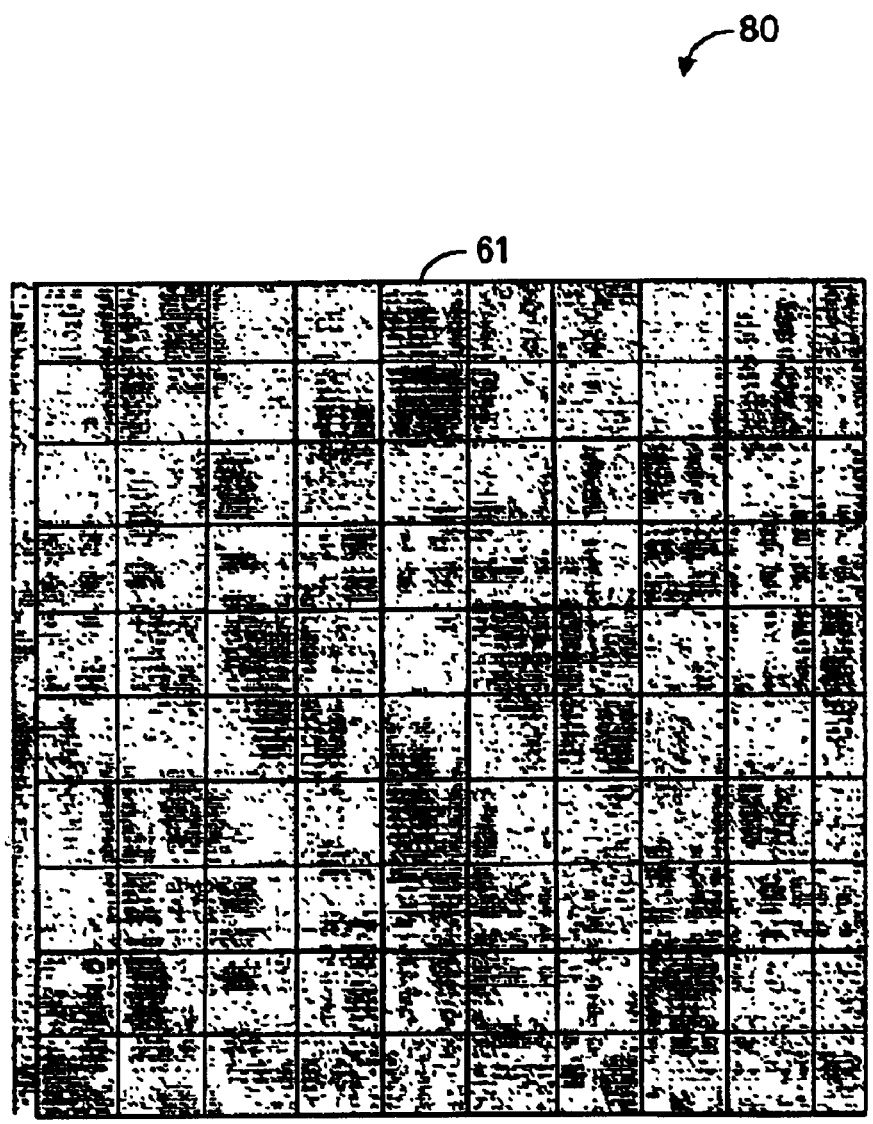
FIG. 8 is a view of a calibration radiation image according to some embodiments of the present invention.

A calibration radiation image of phantom 35 is then acquired in step S608. FIG. 8 is a view of radiation image 80 acquired in step S608. As shown, calibration radiation image 80 does not show a radiation field in alignment with an outer edge of grid pattern 61, as would be the case if the radiation field and light field used to position phantom 35 were congruent. More specifically, calibration radiation image 80 shows vertical alignment of the two fields, but misalignment in the horizontal direction.

In step S609, the radiation image acquired in step S608 is corrected using the reference radiation image acquired in step S605 to produce a corrected radiation image. Such correction may proceed by performing gain correction or shading correction. According to gain correction, pixel values of calibration radiation image 80 are normalized based on relative pixel sensitivities reflected in reference radiation image 70. In this regard, intensities of the pixels of reference radiation image 70 are assumed to reflect the pixels' sensitivity to light.

In a simple example of gain correction, an adjustment value corresponding to each pixel of reference radiation image 70 is determined. The adjustment values are determined so that the intensities of each pixel in radiation image 70 are identical when a corresponding adjustment value is added to each pixel. Therefore, the adjustment values corresponding to darker pixels may be negative and the adjustment values corresponding to lighter pixels may be positive.

Figure 9:
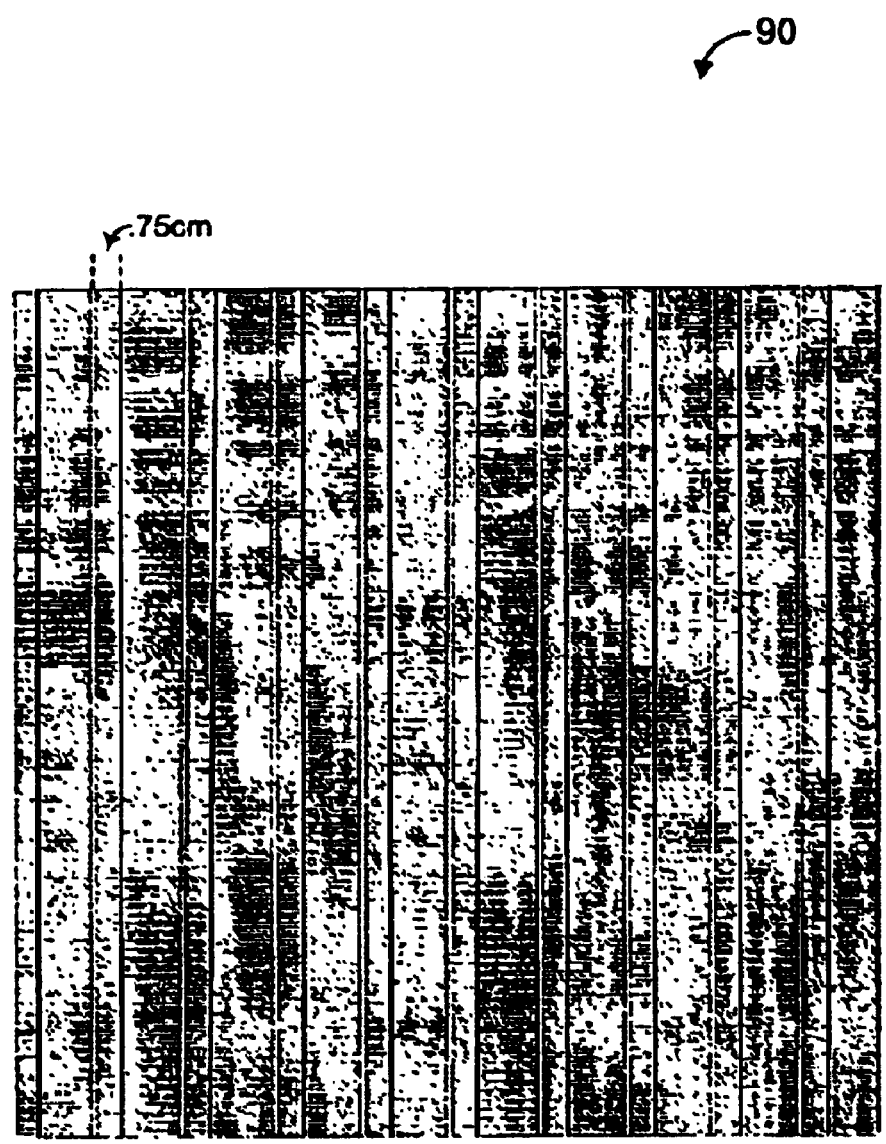
FIG. 9 is a view of a gain-corrected radiation image according to some embodiments of the present invention.

According to the simple example, the above-described adjustment values are added to each pixel of calibration radiation image 80 in step S609 to produce a gain-corrected radiation image. FIG. 9 is a view of resulting gain-corrected radiation image 90. As shown, the light lines of image 90 represent grid pattern 61 as reflected in reference radiation image 70. Moreover, corrected image 90 does not include any noticeable horizontal lines in the phantom area of calibration radiation image 80 because reference radiation image 70 is in vertical alignment with calibration radiation image 80. In this regard, gain-corrected image 90 would appear substantially homogeneous if reference radiation image 70 was in vertical and horizontal alignment with calibration radiation image 80.

Figure 10:
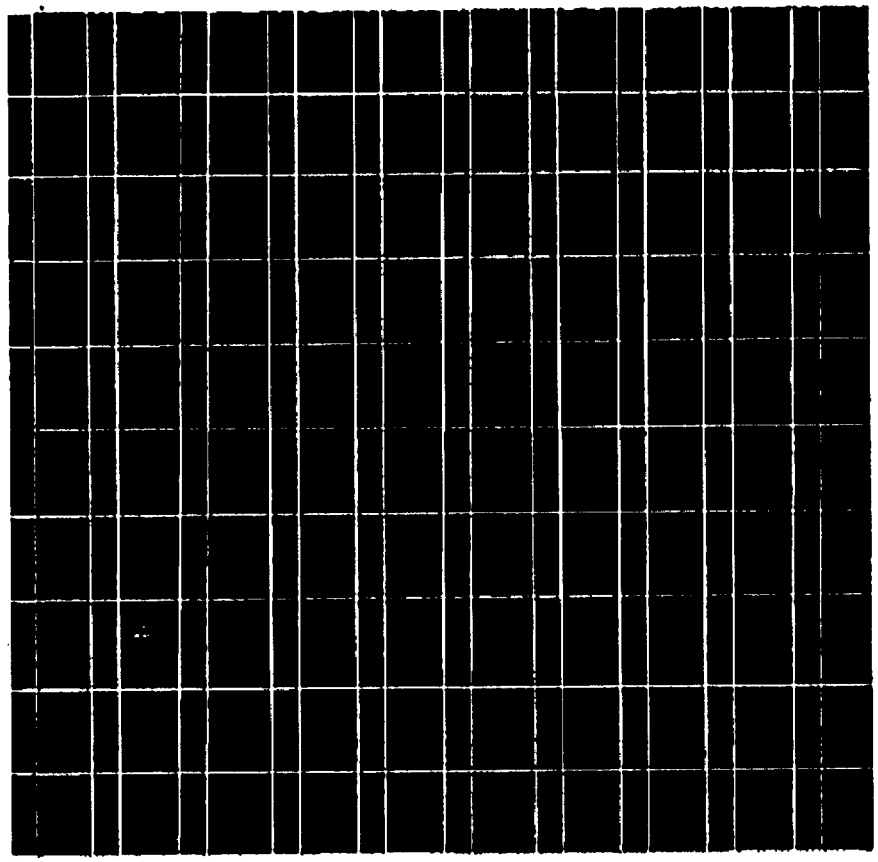
FIG. 10 is a view of a shade-corrected radiation image according to some embodiments of the present invention.

In a case that shading correction is used in step S609, reference radiation image 70 may be subtracted from calibration radiation image 80 to produce a shade-corrected radiation image. Specifically, a value of a pixel of reference radiation image 70 is subtracted from a value of the same pixel of calibration radiation image 80 to determine a new, shade-corrected value for the pixel. This process is repeated for each pixel to create a shade-corrected image. FIG. 10 is a view of shade-corrected radiation image 100 according to the present example. It should be noted that leveling techniques may be used to enhance contrast between light, gray and dark pixels of gain-corrected radiation image 90 and to enhance contrast between gray and dark pixels of shade-corrected radiation image 100. It should also be noted that any currently or hereafter-known methods of gain correction and/or shade correction may be used in conjunction with the present invention.

The following process steps will be described with respect to gain-corrected radiation image 90, but it should be noted that the descriptions are easily altered to enable execution of the process steps with respect to shade-corrected radiation image 100.

In step S610, a deviation between the light field of step S606 and the radiation field used in step S608 is determined based on gain-corrected radiation image 90. Because phantom 35 was placed precisely within the light field (or at a known physical relationship from the light field), and because the light field and the radiation field of linac 10 was congruent when reference radiation image 70 was acquired, this deviation may be determined by measuring a misalignment between grid pattern 61 as reflected in reference radiation image 70 and grid pattern 61 as reflected in calibration radiation image 80. This misalignment may be measured using radiation image 90.

More particularly, radiation image 90 shows that the vertical grid lines reflected in calibration radiation image 80 are shifted 0.75 cm to the right of corresponding grid lines reflected in reference radiation image 70. Such misalignment indicates a 0.75 cm horizontal deviation between the light field and the radiation field at imaging device 20. Of course, magnification effects due to spread of the radiation beam should be taken into account when determining a deviation at the location of phantom 35 which corresponds to this 0.75 cm deviation. The present example shows deviation in only one dimension, but it should be noted that similar techniques may be used to determine two-dimensional deviations. Moreover, in a case that the position at which phantom 35 is placed in step S605 is different from the position at which phantom 35 is placed in step S607, the deviation can be determined as described above by also taking into account a physical relationship between the two positions.

Figure 11:
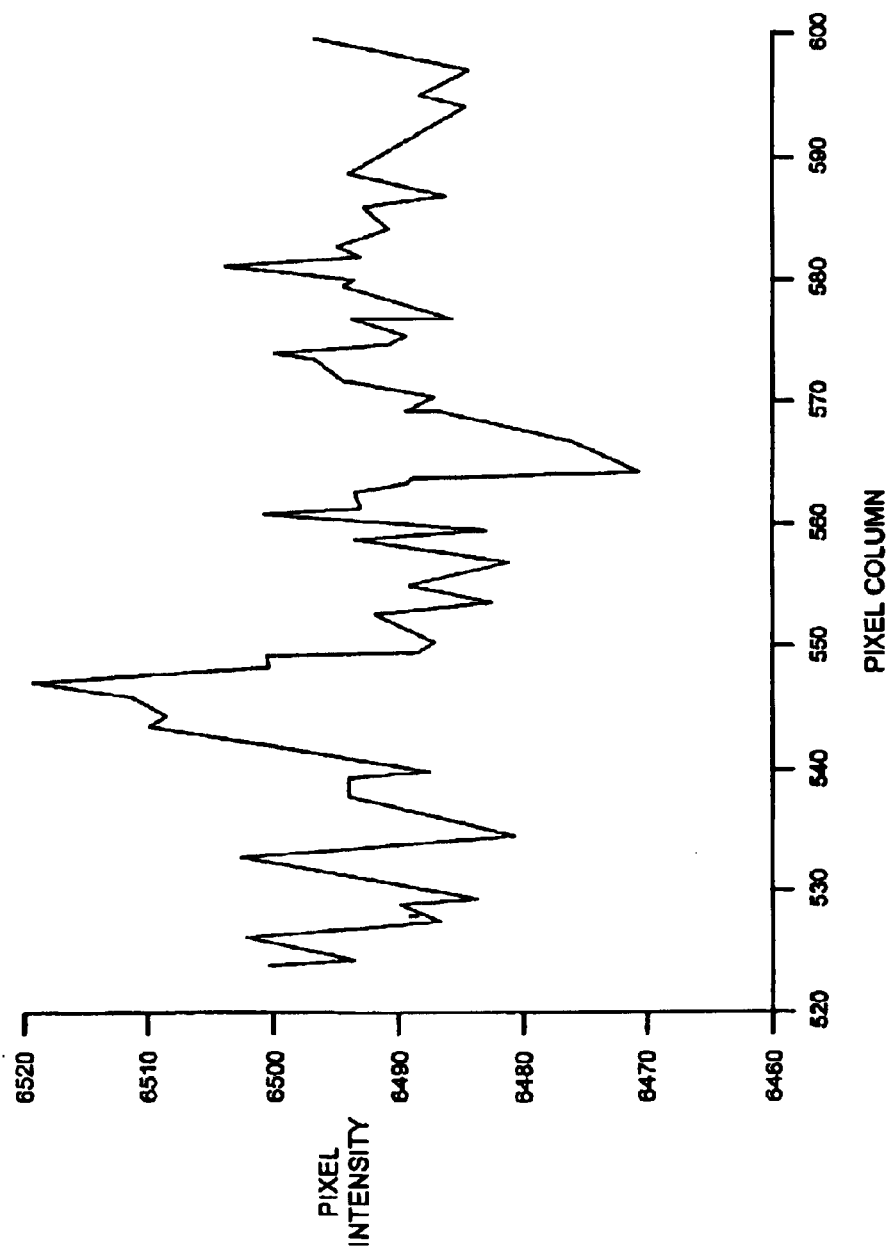
FIG. 11 is a chart for determining deviation between a light field and a radiation field according to some embodiments of the present invention.

FIG. 11 shows graph 1100 that is used to determine a deviation according to some embodiments of step S610. Graph 1100 is based on gain-corrected radiation image 90, and plots pixel intensities for each pixel column of a portion of a single horizontal line. The peaks in pixel intensity represent the light vertical lines of image 90, while the valleys represent the dark vertical lines. To determine field deviation, a number of pixel columns between a peak and a valley is determined and the number is multiplied by a known width per pixel column. In some embodiments, this width is approximately 400 microns, therefore a ten pixel deviation corresponds to a 0.4 cm deviation.

In step S611, it is then determined whether the determined deviation is within specified tolerances. If not, relative positions of the radiation field and the light field are adjusted in step S612 based on the determined deviation in order to bring the deviation within the specified tolerances. In some embodiments, these relative positions are adjusted by adjusting the light field only. The positions may be adjusted in some embodiments by adjusting the radiation field or both the light field and the radiation field. Flow then returns to step S608 from step S612 and continues as described above. Process steps 600 terminate once it determined in step S611 that the determined deviation is within the specified tolerances. Radiation treatment according to the treatment plan may then proceed.

Many of process steps 600 may be performed automatically. In this regard, phantom 35 may be embedded within table 30 and/or automatically placeable at the isocenter using a mechanical device. In these embodiments, steps S606 through S612 may be performed automatically, with the determination in step S610 being determined using image processing techniques and with the adjustment in step S612 being automated based on the determined deviation. Of course, steps S601 through S605 are also performed automatically in some embodiments.

Figure 12A:
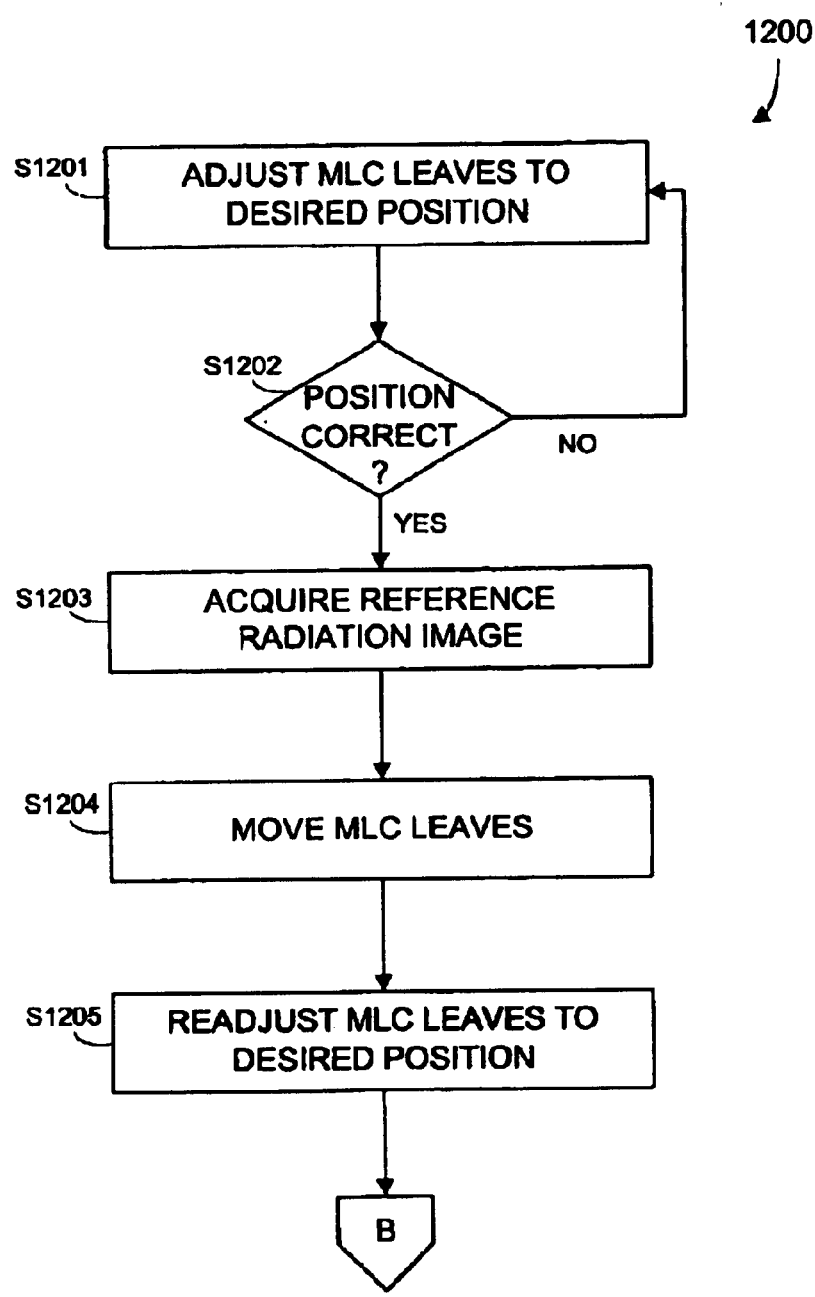
FIGS. 12A and 12B comprise a flow diagram illustrating process steps to verify MLC leaf position according to some embodiments of the present invention.
Figure 12B:
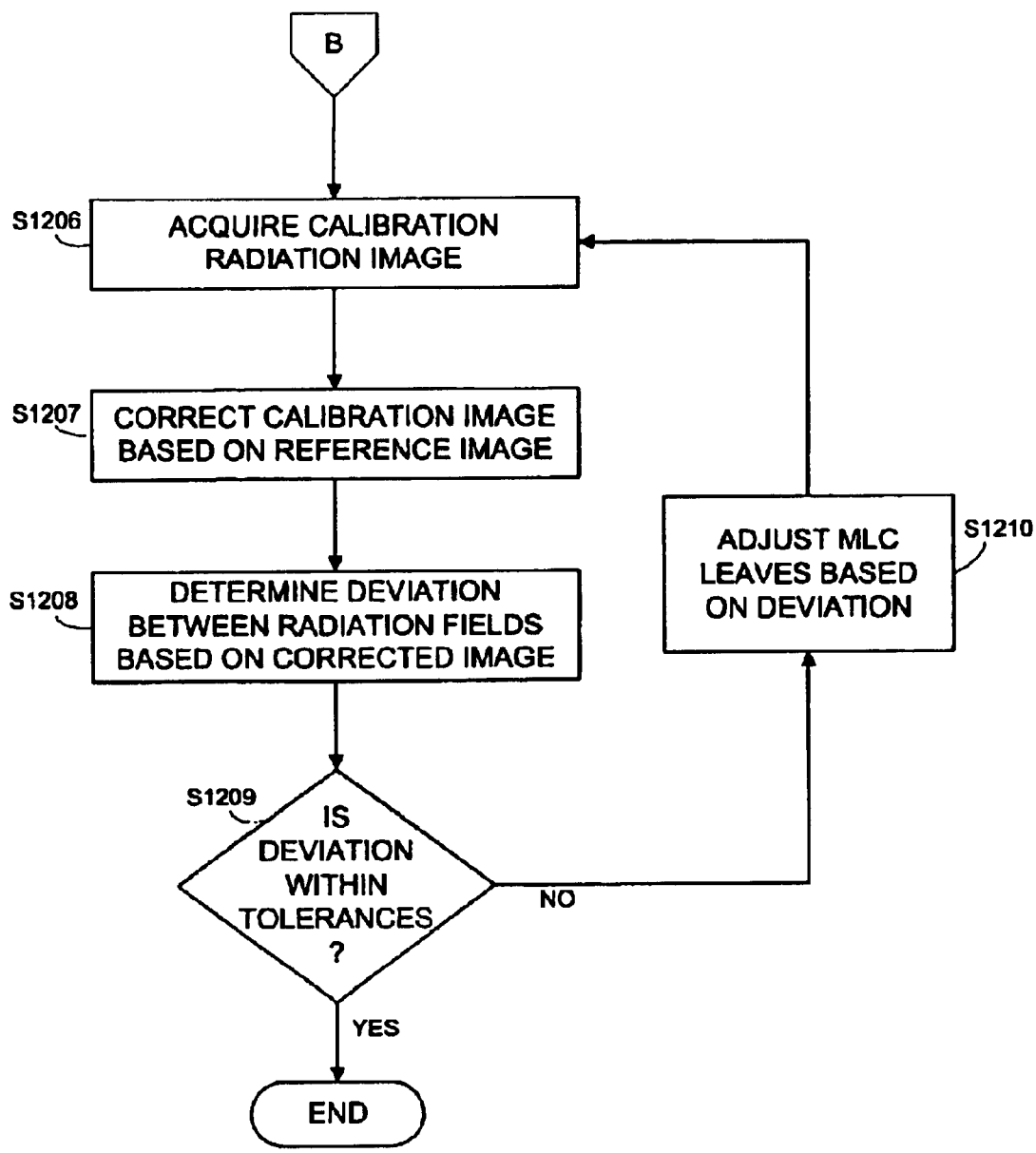

FIGS. 12A and 12B comprise a flow diagram of process steps 1200 according to some embodiments of the invention. Process steps 1200 may be embodied by hardware and/or software of processor 41, linac 10, imaging device 20, and/or another device in direct or indirect communication with imaging device 20. Briefly, process steps 1200 provide for confirming the position of collimator leaves prior to radiation treatment.

Leaves 48 of collimator 47 are moved to a desired position in step S1201. In the present example of step S1201, a suitable accessory is first inserted into a slot of accessory tray 13. Firmware included in the accessory, Linac 10, or another connected device is executed to move leaves 48 to a position that creates a diamond-shaped opening through which light and radiation may pass. Moreover, jaws 46*a* and 46*b* are opened wide enough so that a resulting radiation or light field emitted from treatment head 11 is defined solely by leaves 48. Other leaf positions may be used in conjunction with the present invention, some of which use one or more of jaws 46*a* and 46*b* in addition to leaves 48 to define the radiation and light fields.

The leaf position is verified in step S1202. In one conventional method, the leaf position is verified by attaching a sheet of paper to treatment head 11 so that the sheet lies between collimator 47 and table 30. A pattern is printed on the sheet that shows the perimeter of a light field that is produced if leaves 48 are in the desired position. Accordingly, the sheet may be provided by a manufacturer of the accessory that is inserted in accessory tray 13. The position is verified by turning on light bulb 29 and by verifying that the perimeter of the resulting light field matches the perimeter printed on the sheet. If the position is correct, flow returns to step S1201. If not, flow proceeds to step S1203. It should be noted that other methods for verifying the leaf position may be employed in step S1202.

Figure 13:
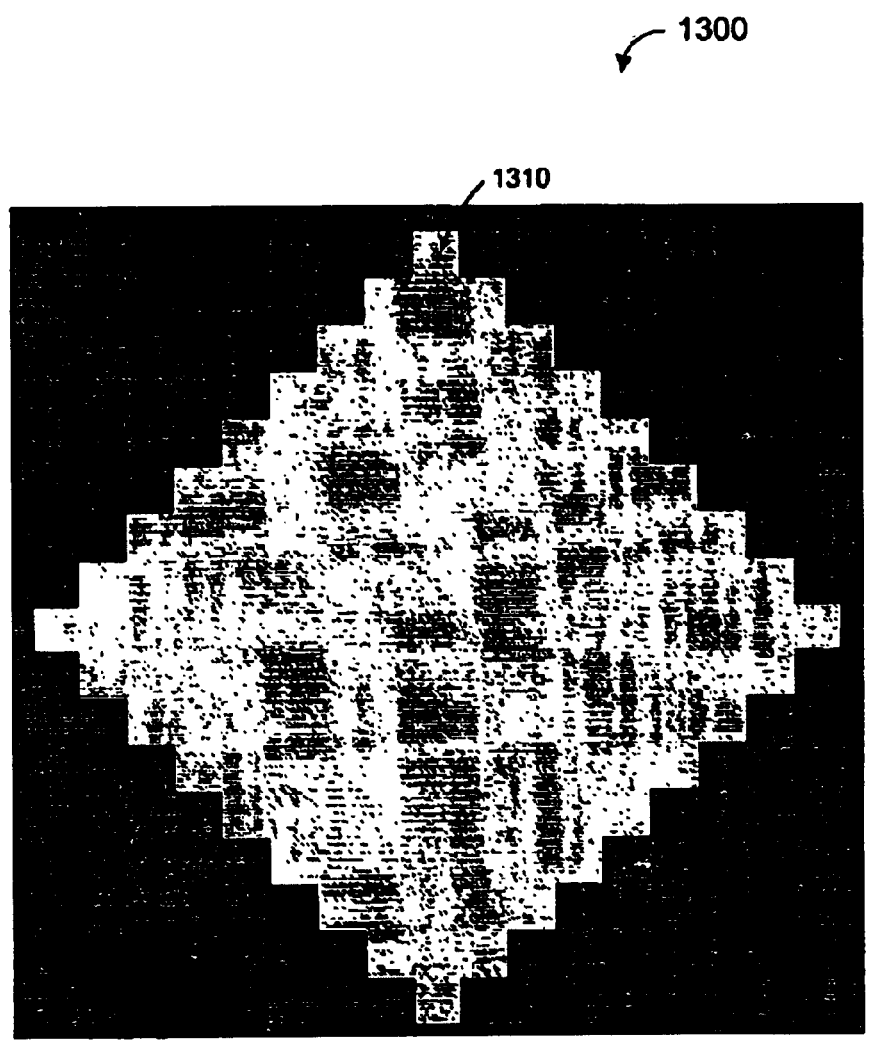
FIG. 13 is a view of a reference radiation image according to some embodiments of the present invention.

A reference radiation image is acquired in step S1203. The reference radiation image is acquired by activating radiation emitter 28 and by acquiring electronic image data representing a radiation field emitted by radiation emitter 28 and shaped by one or more of leaves 48. FIG. 13 is a view of reference radiation image 1300 acquired according to some embodiments of step S1203. As shown, a radiation field shaped by leaves 48 appears as lighter area 1310 in the acquired image. It should be noted that steps S1201 through S1203 may be performed anytime before radiation treatment, but are commonly obtained in the early morning prior to the administration of several radiation treatments throughout the day.

Accordingly, the configuration of leaves 48 may change one or more times during step S1204 for testing, training and/or treatment. At some point, however, an operator determines to use the diamond-shaped pattern and to verify the position of leaves 48 prior to using the diamond-shaped pattern. Collimator 47 is then adjusted in step S1205 so that leaves 48 are moved to the desired position that will produce the diamond-shaped radiation field. Next, in step S1206, a calibration radiation image is acquired in the same manner as described with respect to step S1203.

Figure 14:
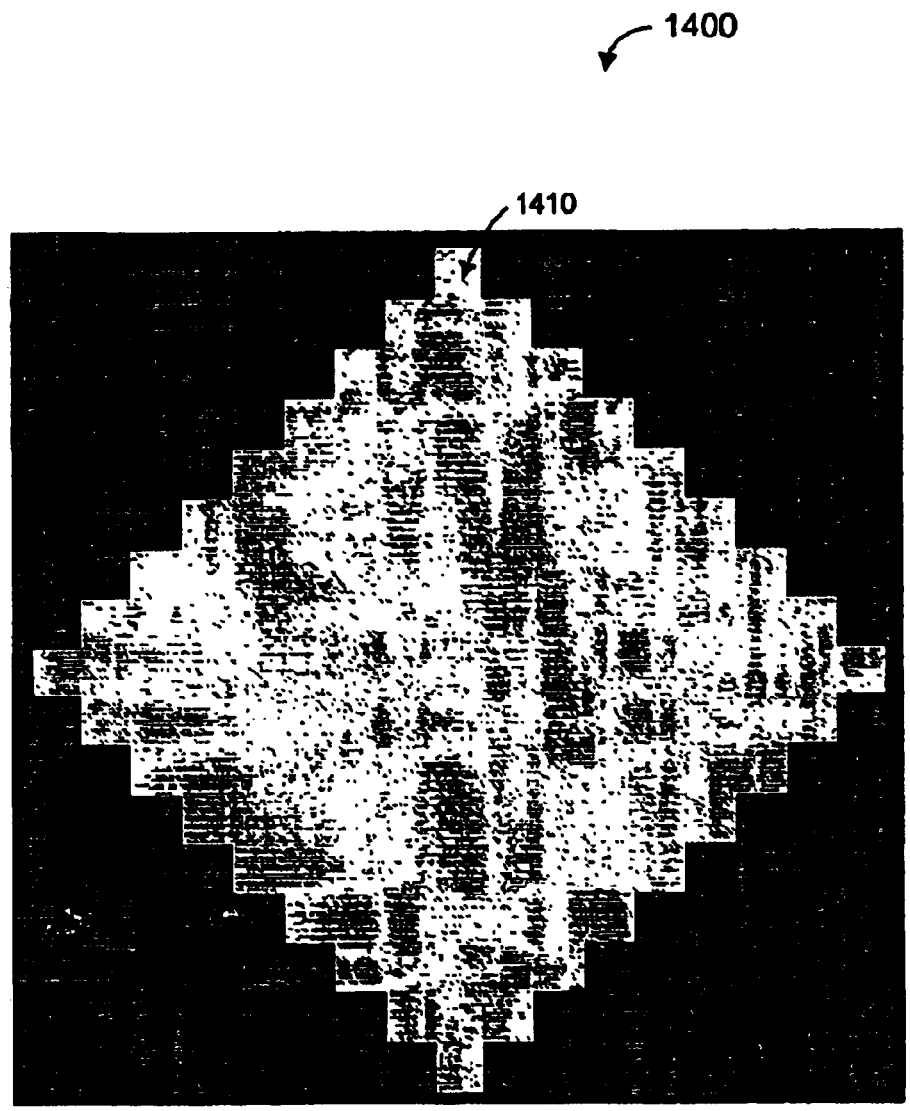
FIG. 14 is a view of a calibration radiation image according to some embodiments of the present invention.

FIG. 14 shows such calibration image 1400 acquired in step S1206. Although it is difficult to discern by looking at FIG. 14, light area 1410 is larger than light area 1310 of FIG. 13 in the present example. This larger size indicates that the radiation field of step S1206 is larger than the radiation field of step S1203 and that leaves 48 are therefore configured differently than they were in step S1203.

Figure 15:
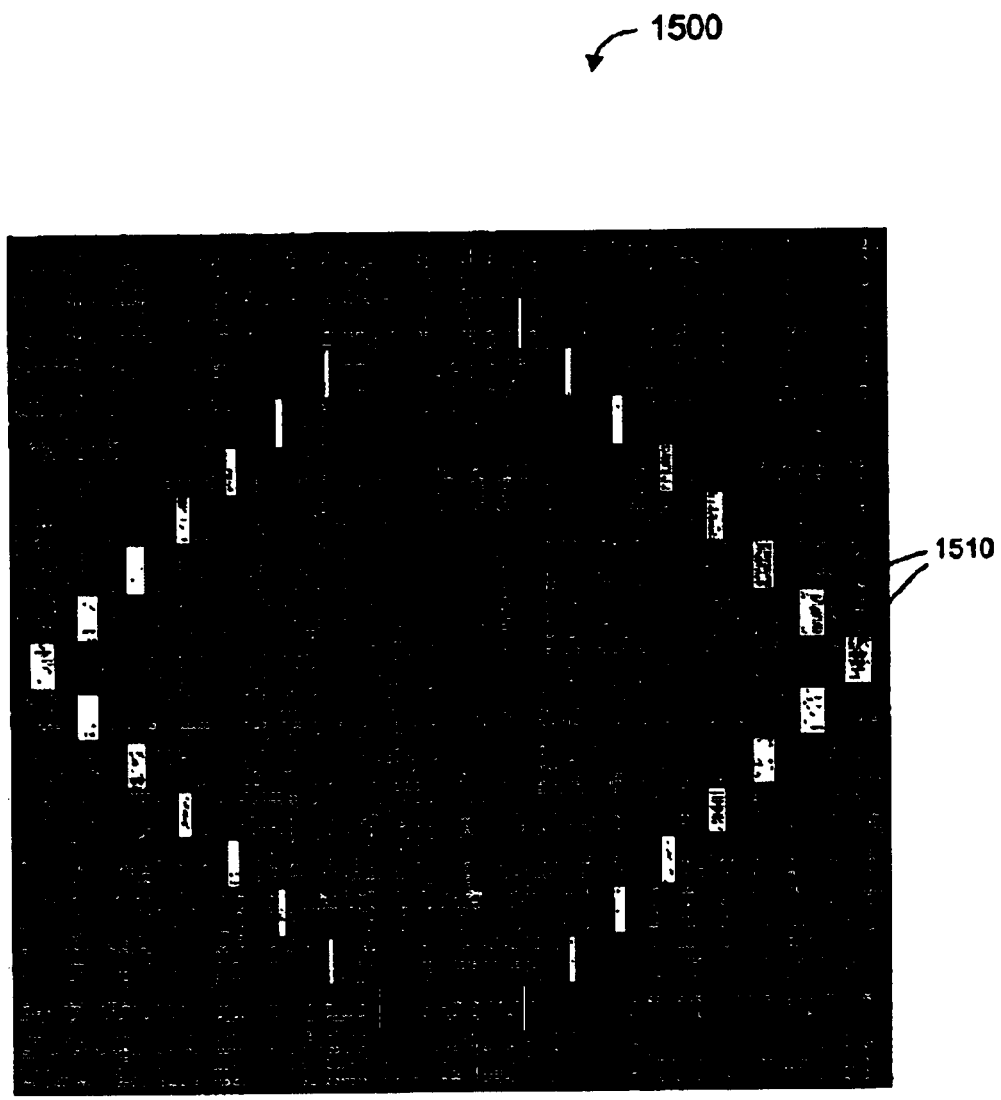
FIG. 15 is a view of a shade-corrected radiation image according to some embodiments of the present invention.

Calibration radiation image 1400 is corrected in step S1207 based on reference radiation image 1300. As described above, shade correction or gain correction may be used to perform this correction. FIG. 15 illustrates shade-corrected image 1500 that results from performing shade correction on image 1400 based on image 1300. A deviation between the radiation field represented in image 1400 and the radiation field represented in image 1300 is then determined in step S1208 based on shade-corrected image 1500.

The deviation is represented by streaks 1510 in shade-corrected image 1500. More particularly, because area 1410 is larger than area 1310, some pixels are dark in image 1400 and light in image 1300. When image 1300 is subtracted from image 1400 according to the present example of shade correction, these pixels become light-colored in the corrected image, while all other pixels that have similar or identical values become dark-colored. As shown in FIG. 15, streaks 1510 may indicate that some of leaves 48 are in a same position in step S1206 as they were in step S1203, while others of leaves 48 may be in different positions.

The deviation may be determined by measuring the dimensions of streaks 1510 and by factoring in magnifications caused by spread of the radiation beam between leaves 48 and imaging device 20. Alternatively, the deviation may be determined based on a known pixel size and on a graph of pixel intensities such as that shown in FIG. 11.

Using the shade-correction technique of the present example, corrected radiation image 1500 would consist completely of dark pixels if the leaf configuration in step S1206 was identical to the leaf configuration of step S1203. If the above-described gain correction technique is used in step S1208, a corrected image corresponding to identical leaf configurations would consist entirely of light pixels. The gain-corrected image would further include black streaks if the configurations were not identical. In this regard, the image would comprise a negative of image 1500 of FIG. 15.

In step S1209, it is determined whether the determined deviation is within specified tolerances. If not, leaves 48 are adjusted based on the determined deviation in step S1210 and flow thereafter returns to step S1206. Flow terminates after it is determined in step S1209 that the deviation is within the specified tolerances, and treatment may then follow. It should be noted that the adjustment of step S1210 may be performed without operator intervention based on the determined deviation, and that some or all other of process steps 1200 may be performed automatically.

Those in the art will appreciate that various adaptations and modifications of the above-described embodiments can be configured without departing from the scope and spirit of the invention. For example, embodiments of the present invention may differ from process steps 600 and 1200. Therefore, it is to be understood that, within the scope of the appended claims, the invention may be practiced other than as specifically described herein.

What is claimed is:

1. A method comprising:
   confirming congruence of a light field emitted by a light emitter and a radiation field emitted by a radiation emitter;
   acquiring first electronic image data representing a phantom located at a first position and irradiated by a second radiation field emitted by the radiation emitter;
   acquiring second electronic image data representing the phantom located at a second position based at least on a second light field emitted by the light emitter and irradiated by a third radiation field emitted by the radiation emitter;
   generating third electronic image data by correcting the second electronic image data based at least on the first electronic image data; and
   determining a deviation between the second light field and the third radiation field based at least on the third electronic image data.

2. A method according to claim 1, wherein the phantom includes a pattern and wherein each of the first and second electronic image data reflects the pattern.

3. A method according to claim 2, wherein the determining step comprises:
identifying, in the third electronic image data, the pattern as reflected by the first electronic image data;
identifying, in the third electronic image data, the pattern as reflected by the second electronic image data; and
measuring a misalignment between the identified pattern as reflected by the first electronic image data and the identified pattern as reflected by the second electronic image data.

4. A method according to claim 1, further comprising:
prior to acquiring the first electronic data and after confirming congruence of the light field and the radiation field, positioning the phantom at the first position based on the light field.

5. A method according to claim 1, wherein the first position and the second position are substantially identical.

6. A method according to claim 1, wherein a physical relationship between the first position and the second position is known.

7. A method according to claim 1, further comprising:
adjusting a relationship between the second light field and the third radiation field based on the deviation.

8. A method according to claim 1, wherein the step of correcting comprises:
performing gain correction on the second electronic image data using the first electronic image data as a gain correction image.

9. A method according to claim 1, wherein the step of correcting comprises:
correcting the second electronic image data for pixel sensitivities, wherein the pixel sensitivities are represented by the first electronic image data.

10. A method according to claim 1, wherein the step of correcting comprises:
performing shade correction on the second electronic image data using the first electronic image data as a shade correction image.

11. A method according to claim 1, wherein the step of correcting comprises:
correcting the second electronic image data for one or more of lens vignetting and optical scattering, wherein the one or more of lens vignetting and optical scattering are represented by the first electronic image data.

12. A method comprising:
confirming a first leaf configuration of multi-leaf collimator leaves;
acquiring first electronic image data representing a first radiation field emitted by a radiation emitter and shaped by one or more of the multi-leaf collimator leaves in the first leaf configuration;
moving one or more of the multi-leaf collimator leaves from the first leaf configuration;
moving one or more of the multi-leaf collimator leaves to a second leaf configuration;
acquiring second electronic image data representing a second radiation field emitted by the radiation emitter and shaped by one or more of the multi-leaf collimator leaves in the second leaf configuration;
generating third electronic image data by correcting the second electronic image data based at least on the first electronic image data; and
determining a deviation between the first radiation field and the second radiation field based at least on the third electronic image data.

13. A method according to claim 12, further comprising:
moving the multi-leaf collimator leaves from the second position to the first position based at least on the deviation between the first radiation field and the second radiation field.

14. A method according to claim 12, further comprising:
determining a deviation between the first leaf configuration and the second leaf configuration based on the deviation between the first radiation field and the second radiation field; and
moving the multi-leaf collimator leaves from the second position to the first position based at least on the deviation between the first leaf configuration and the second leaf configuration.

15. A method according to claim 12, wherein the first position and the second position are substantially identical.

16. A method according to claim 12, wherein a physical relationship between the first position and the second position is known.

17. A method according to claim 12, wherein the step of generating comprises:
performing gain correction on the second electronic image data using the first electronic image data as a gain correction image.

18. A method according to claim 12, wherein the step of generating comprises:
correcting the second electronic image data for pixel sensitivities, wherein the pixel sensitivities are represented by the first electronic image data.

19. A method according to claim 12, wherein the step of generating comprises:
performing shade correction on the second electronic image data using the first electronic image data as a shade correction image.

20. A method according to claim 12, wherein the step of generating comprises:
correcting the second electronic image data for one or more of lens vignetting and optical scattering, wherein the one or more of lens vignetting and optical scattering are represented by the first electronic image data.

21. A computer-readable medium storing computer-executable process steps, the process steps comprising:
a step to confirm congruence of a light field emitted by a light emitter and a radiation field emitted by a radiation emitter;
a step to acquire first electronic image data representing a phantom located at a first position and irradiated by a second radiation field emitted by the radiation emitter;
a step to acquire second electronic image data representing the phantom located at a second position and irradiated by a third radiation field emitted by the radiation emitter;
a step to generate third electronic image data by correcting the second electronic image data based at least on the first electronic image data; and
a step to determine a deviation between the second light field and the third radiation field based at least on the third electronic image data.

22. A computer-readable medium storing computer-executable process steps, the process steps comprising:
a step to confirm a first leaf configuration of multi-leaf collimator leaves;

a step to acquire first electronic image data representing a first radiation field emitted by a radiation emitter and shaped by one or more of the multi-leaf collimator leaves in the first leaf configuration;

a step to move one or more of the multi-leaf collimator leaves from the first leaf configuration;

a step to move one or more of the multi-leaf collimator leaves to a second leaf configuration;

a step to acquire second electronic image data representing a second radiation field emitted by the radiation emitter and shaped by one or more of the multi-leaf collimator leaves in the second leaf configuration;

a step to generate third electronic image data by correcting the second electronic image data based at least on the first electronic image data; and a step to determine a deviation between the first radiation field and the second radiation field based at least on the third electronic image data.

23. An apparatus comprising:

a memory storing processor-executable process steps;

a processor in communication with the memory and operative in conjunction with the stored process steps to:

confirm congruence of a light field emitted by a light emitter and a radiation field emitted by a radiation emitter;

acquire first electronic image data representing a phantom located at a first position and irradiated by a second radiation field emitted by the radiation emitter;

acquire second electronic image data representing the phantom located at a second position and irradiated by a third radiation field emitted by the radiation emitter;

generate third electronic image data by correcting the second electronic image data based at least on the first electronic image data; and determine a deviation between the second light field and the third radiation field based at least on the third electronic image data.

24. An apparatus comprising:

a memory storing processor-executable process steps;

a processor in communication with the memory and operative in conjunction with the stored process steps to:

confirm a first leaf configuration of multi-leaf collimator leaves;

acquire first electronic image data representing a first radiation field emitted by a radiation emitter and shaped by one or more of the multi-leaf collimator leaves in the first leaf configuration;

move one or more of the multi-leaf collimator leaves from the first leaf configuration;

move one or more of the multi-leaf collimator leaves to a second leaf configuration;

acquire second electronic image data representing a second radiation field emitted by the radiation emitter and shaped by one or more of the multi-leaf collimator leaves in the second leaf configuration;

generate third electronic image data by correcting the second electronic image data based at least on the first electronic image data; and determine a deviation between the first radiation field and the second radiation field based at least on the third electronic image data.

25. A system comprising:

a light emitter for emitting light;

a radiation emitter for emitting radiation;

a data acquisition device for acquiring image data based on the emitted radiation;

a phantom; and an image processing device, wherein the data acquisition device acquires first electronic image data representing the phantom located at a first position and irradiated by a first radiation field emitted by the radiation emitter, acquires second electronic image data representing the phantom located at a second position based on a light field emitted by the light emitter and irradiated by a second radiation field emitted by the radiation emitter, and wherein the image processing device generates third electronic image data by correcting the second electronic image data based at least on the first electronic image data, and determines a deviation between the light field and the second radiation field based at least on the third electronic image data.

26. A system comprising:

a light emitter for emitting light;

a radiation emitter for emitting radiation;

a multi-leaf collimator comprising leaves for shaping a radiation field emitted by the light emitter;

a data acquisition device for acquiring image data based on the emitted radiation; and an image processing device, wherein the data acquisition device acquires first electronic image data representing a first radiation field emitted by the radiation emitter and shaped by one or more of the multi-leaf collimator leaves in a first leaf configuration, acquires second electronic image data representing a second radiation field emitted by the radiation emitter and shaped by one or more of the multi-leaf collimator leaves in a second leaf configuration, and wherein the image processing device generates third electronic image data by correcting the second electronic image data based at least on the first electronic image data, and determines a deviation between the first radiation field and the second radiation field based at least on the third electronic image data.

* * * * *